United States Patent [19]

Kohayakawa et al.

[11] Patent Number: 4,600,012
[45] Date of Patent: Jul. 15, 1986

[54] APPARATUS FOR DETECTING ABNORMALITY IN SPINAL COLUMN

[75] Inventors: Yoshimi Kohayakawa; Machiko Matsushita, both of Yokohama, Japan

[73] Assignee: Canon Kabushiki Kaisha, Tokyo, Japan

[21] Appl. No.: 725,547

[22] Filed: Apr. 22, 1985

[51] Int. Cl.⁴ .............................................. A61B 5/10
[52] U.S. Cl. ................................. 128/665; 128/781; 358/107
[58] Field of Search ............... 128/665, 774, 781, 782, 128/653; 33/174 D; 356/2; 358/107

[56] References Cited

U.S. PATENT DOCUMENTS 3,218,389 11/1965 Reed ..................................... 358/107
3,533,684 10/1970 Stark et al. ...................... 358/107 X
3,551,052 12/1970 Reiber ............................. 358/107 X

FOREIGN PATENT DOCUMENTS 1211962 3/1960 France ............................. 128/781

Primary Examiner—Kyle L. Howell
Assistant Examiner—John C. Hanley
Attorney, Agent, or Firm—Fitzpatrick, Cella, Harper & Scinto

[57] ABSTRACT

An apparatus for detecting abnormality in a spinal column is provided with means for projecting at least a slit-like light which is parallel to the imaginary spinal line on each of right and left sides of the back of an inspected person, pickup means for taking the image of the left and right backs of the inspected person, and a signal processing unit for detecting and comparing the positions of the slit-like lights on the right and left shoulders by means of the scanning lines of the pickup means.

9 Claims, 8 Drawing Figures

APPARATUS FOR DETECTING ABNORMALITY IN SPINAL COLUMN

BACKGROUND OF THE INVENTION

1. Field of the Invention

The present invention relates to an apparatus for detecting abnormality in the spinal column, and more particularly to such apparatus for detecting a spinal abnormality such as lateral spinal curvature or scoliosis.

2. Description of the Prior Art

Conventionally abnormalities in the spinal column such as lateral spinal curvature are detected, not only by visual inspection or probing by a doctor, but also either by a moire method in which the body surface, particularly the back, of an inspected person is illuminated with light through two gratings and the unbalance in the configuration of the body of the inspected person is detected through the interference pattern formed on the body surface, or by a low X-ray method in which the inspected person is irradiated with a low X-ray to directly photograph the spinal column. However, in any of these methods, the detection requires experience, and objective data are difficult to obtain because of fluctuations in diagnoses by the diagnosing persons, as consistent diagnoses of many persons in a consecutive manner is difficult to achieve. In addition, the moire method, requiring large equipment, lacks mobility and is therefore unsuitable for collective diagnosis for example of children in a school, while the X-ray photographing method requires expensive equipment and poses a problem of exposure to X-ray in children.

SUMMARY OF THE INVENTION

An object of the present invention is to provide a spinal abnormality detecting apparatus capable of providing stable results.

Another object of the present invention is to provide a spinal abnormality detecting apparatus capable of detecting the difference in the degree of elevation in the right and left halves of the back of the inspected person in a forward bent posture of said person.

DESCRIPTION OF THE PREFERRED EMBODIMENTS

Figure 1:
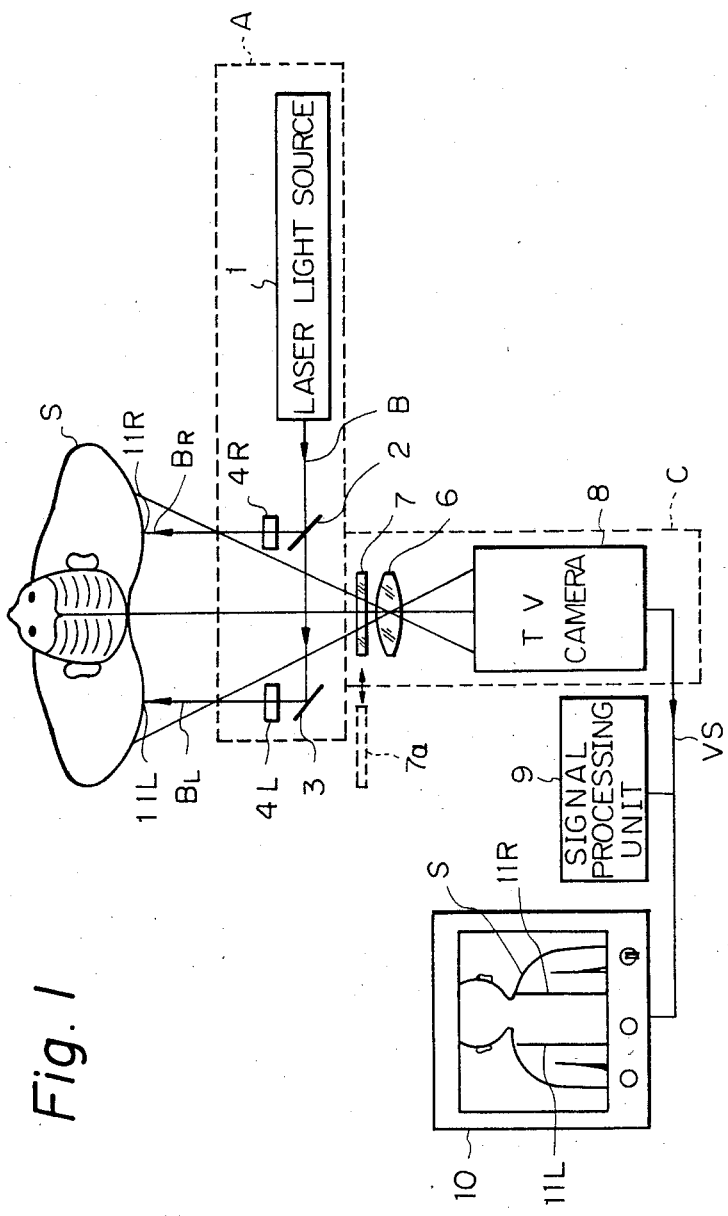
FIG. 1 is a schematic view of an embodiment of the present invention.

Now the present invention will be clarified in detail by an embodiment thereof shown in the attached drawings. FIG. 1 is a schematic plan view of an apparatus for detecting the spinal abnormality in an inspected person S, constituting an embodiment of the present invention.

Along the path of a laser beam B emitted by a laser unit 1, there is provided a half mirror 2 for splitting said beam into a right beam $B_R$ and a left beam $B_L$. Along the path of the beam $B_R$ reflected by the half mirror 2 there is provided a cylindrical lens 4R, and, along the path of the beam $B_L$ transmitted by the half mirror 2 there are provided a mirror 3 for rectangularly deflecting the beam $B_L$ to guide the same parallel to the right beam $B_R$, and a cylindrical lens 4L. The above-described optical members 1, 2, 3, 4R and 4L constitute an illuminating system A of the present apparatus. Slit-like lights may be formed by incandescent lamps, slits and diaphragms instead of the laser unit 1 and the cylindrical lenses 4R, 4L or formed by vertical scanning of the laser beam with a galvanometer. Also more information can be obtained by forming two or more light beams on each side of the back instead of a light beam on each side.

At the center between the beams $B_R$ and $B_L$ and behind the half mirror 2 and the mirror 3 there are provided a filter 7 which is movable to a position 7a, a television lens 6 and a television camera 8. The output video signal $V_S$ of the television camera 8 is supplied to a signal processing unit 9 and a monitor television 10 to be explained later. The optical members 6, 7 and 8 constitute an imaging system C of the present apparatus.

The function of the present embodiment is as follows. An inspected person S is positioned in a forward bent posture, in such a manner that the imaginary spinal line or the central axis of the body lies on the central line of the imaging system C. The inspected person S is preferably positioned parallel to the lenses 4R and 4L.

The laser beam B emitted from the laser unit 1 is reflected by the half mirror 2 and the mirror 3, then focused as vertically extended beams $B_R$, $B_L$ parallel to the imaginary spinal line by means of the cylindrical lenses, 4R, 4L and projected onto the back of the inspected person S. If the inspected person S has a spinal abnormality such as lateral spinal curvature, there results a difference in the heights of left and right shoulders in the forward bent posture.

Figure 2:
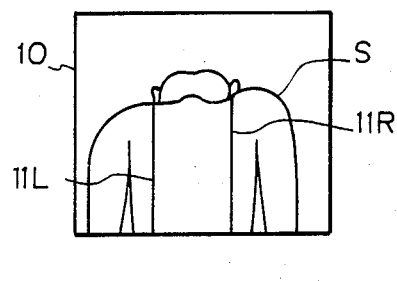
FIGS. 2 and 3 are schematic views of projected images of the beams.

FIG. 2 shows the images, on the monitor television 10, of beams 11R, 11L respectively on the right and left halves of the back of the inspected person S, indicating the presence of a difference between the heights of right and left shoulders of the inspected person S and thus suggesting the presence of a spinal abnormality such as lateral spinal curvature. It is to be noted that FIG. 2 shows the image on the monitor television 10 when the filter 7 in FIG. 1 is at a position 7a.

Figure 3:
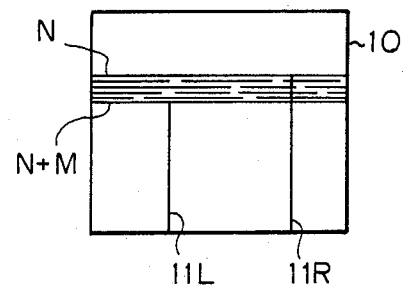
Figure 4:
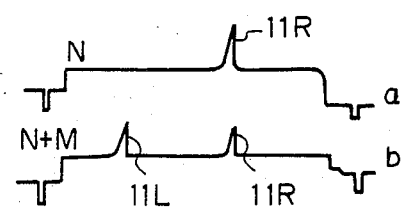
FIG. 4 is a wave form chart showing a video signal.

When the filter 7 in FIG. 1 is positioned in the optical path of the imaging system C as represented by full lines, there are then obtained the images of the beams 11R, 11L alone as shown in FIG. 3. In FIG. 3, the right beam image 11R extends from an N-th scanning line to the last scanning line, while the left beam image 11L extends from an (N+M)-th scanning line. FIG. 4 shows the video signals of the N-th scanning line a and the (N+M)-th scanning line b, in which obtained are peak signals corresponding to the irradiation of beams on the back of the inspected person S. These peak signals are detected by a threshold setter 16 to be explained later.

Figure 5:
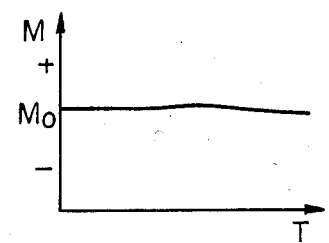
FIGS. 5 and 6 are charts showing the counts of scanning lines.
Figure 6:
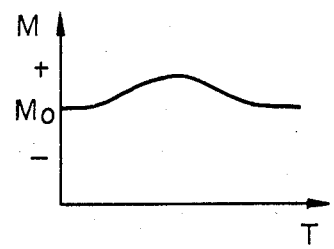

FIGS. 5 and 6 are charts, obtained on two inspected persons, showing the difference in heights of right and left shoulders or the number M of scanning lines when the inspected person bends gradually forward over a time T. FIG. 5 indicates a normal spine while FIG. 6 indicates a abnormal spine.

Figure 7:
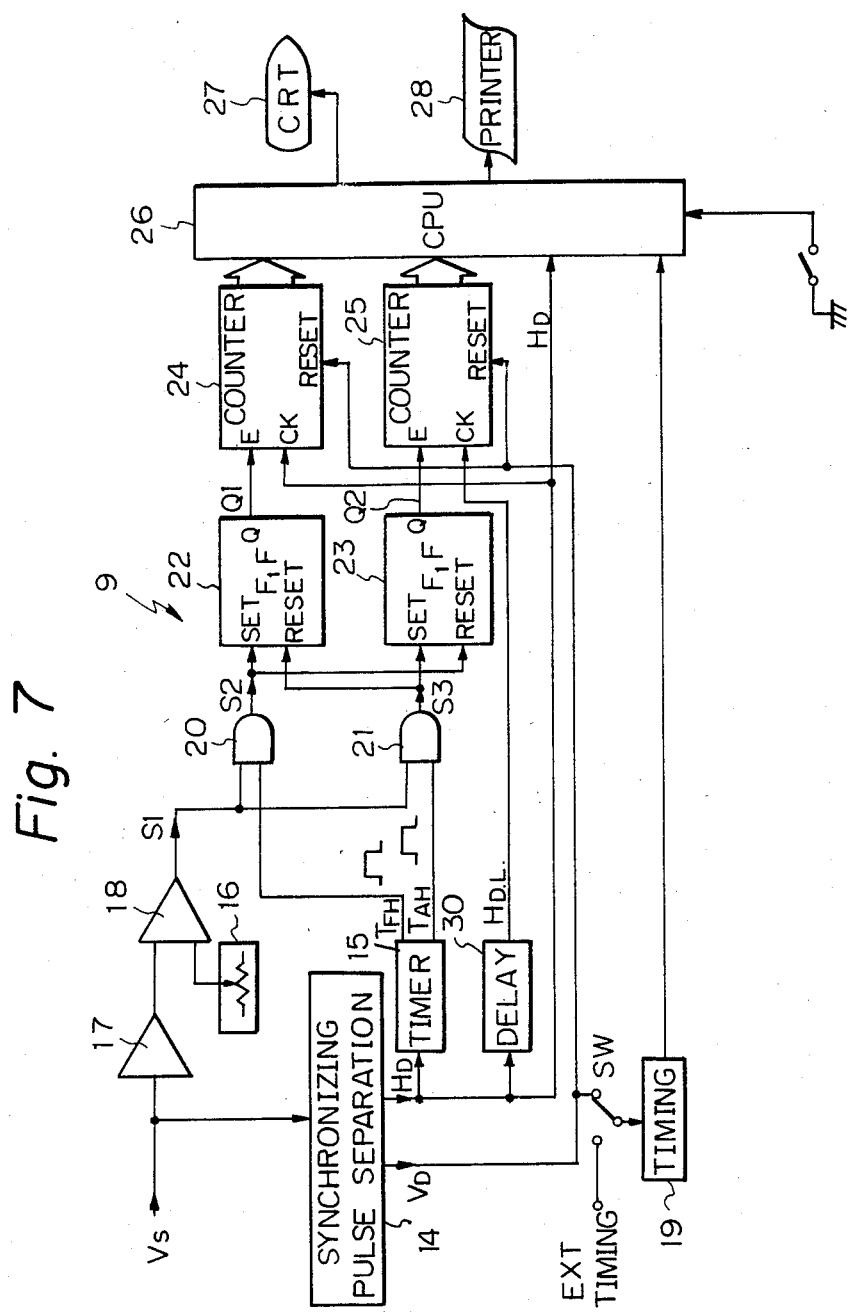
FIG. 7 is a block diagram of a signal processing unit shown in FIG. 1.
Figure 8:
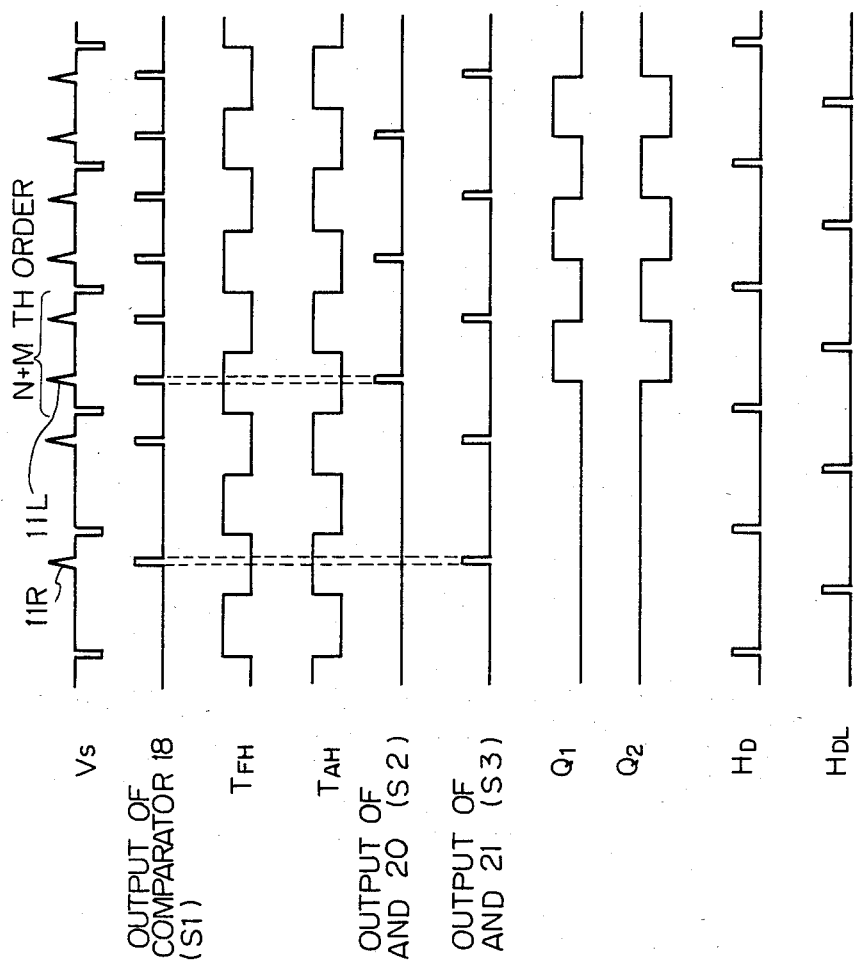
FIG. 8 is a timing chart showing the function of the circuit shown in FIG. 7.

Now reference is made to FIGS. 7 and 8 for explaining the measurement of the height difference between the right and left shoulders of the inspected person S. FIG. 7 is a block diagram of the electric system of the apparatus, corresponding to the signal precessing unit 9 in FIG. 1, and FIG. 8 is a timing chart showing various output signals of the blocks shown in FIG. 7.

A video signal $V_S$ released from the television camera 8 is amplified by an image amplifier 17 and supplied to a binary digitizing comparator 18, which compares said signal with a value determined by a threshold setter 16 for identifying the presence of the laser beam images 11R, 11L on the scanning line, and supplies corresponding signals to AND gates 20, 21.

The video signal $V_S$ is also supplied to a synchronization signal separating circuit 14 to separate the horizonal synchronization signal $H_D$ and the vertical synchronization signal $V_D$. The horizontal synchronization signal $H_D$ is supplied to a beam identifying timer 15, a delay circuit 30, a clock port CK of a counter 24 and a CPU 26 having a buffer memory, and the vertical synchronization signal $V_D$ is supplied to a reset port of the counter 24 and a reset port of another counter 25.

In response to the horizontal synchronization signal $H_D$, the beam identifying timer 15 generates timing pulses $T_{FH}$, $T_{AH}$ (FIG. 8) of a duty ratio of 50%. The timing pulses $T_{FH}$ and $T_{AH}$ have a mutual phase difference of 180° and are respectively supplied to the AND gates 20, 21. The delay circuit 30 generates timing pulses $H_{DL}$ delayed by 180° in phase from the horizontal synchronization signal $H_D$ for supply to the clock port CK of the counter 25.

The output of the AND gate 20 is supplied to a set port of a flip-flop 22 and a reset port of a flip-flop 23, and the output of the AND gate 21 is supplied to a reset port of the flip-flop 22 and a set port of the flip-flop 23. The outputs Q1, Q2 of the Q-ports of the flip-flops 22, 23 are respectively supplied to enable ports E of the counters 24, 25.

When an image as shown in FIGS. 3 and 4 is obtained in the above-described circuit, a video signal $V_S$ as shown in FIG. 8 is obtained from the television camera 8. Said signal $V_S$ is converted, in the comparator 18, into a signal S1 corresponding to the beam images 11R, 11L, and said signal S1 is supplied to the AND gates 20, 21, which form logic products of said signal S1 respectively with the timing pulses $T_{FH}$, $T_{AH}$. Thus the AND gate 21 releases a high-level signal S3 from the N-th scanning line where the beam image 11R first appears, while the AND gate 20 does not release a high-level signal S2. Consequently, the Q-port of the flip-flop 23 alone releases the high-level signal Q2 to the enable port E of the counter 25, which thus initiates the counting of the timing pulses $H_{DL}$.

In the (N+M)-th scanning line where the right and left beam images 11R, 11L appear, also the AND gate 20 releases the signal S2 corresponding to the beam image 11L, whereby the Q-port of the flip-flops 22, 23 respectively release signals Q1 and Q2 repeating high- and low-level states from the signals S1 corresponding to the beam images 11L, 11R, whereby the counter 25 terminates counting at the (N+M)-th scanning line. In case the left shoulder of the inspected person S is higher, the counter 24 counts the horizontal synchronization signal $H_D$ since the beam image appears in the first half of the scanning line of the video signal.

The count M obtained in the above-mentioned manner is supplied to the CPU 26 having a buffer memory controlled by a data sampling timing generator 19, whereby data at various forward bending angles can be obtained by causing the inspected person S to bend forward in a continuous manner.

Such data can be displayed on a cathode ray tube 27 or recorded on a printer 28 as shown in FIGS. 5 and 6. The data shown in FIGS. 5 and 6 are obtained by the continuous forward bending of the inspected person S, but it is also possible to obtain such data by measurements at plural forward bending angles. In such case the timing generator 19 is provided with a selector or change-over switch for entering the timing signal for each forward bending angle.

In the foregoing embodiment, the beam images projected on the back of the inspected person are received by a television camera for counting the number of scanning lines, but it is also possible to use other imaging or pick up means such as a charge-coupled device.

We claim:

1. An apparatus for detecting an abnormality in the spinal column of a patient, comprising:
    means for projecting at least two lines of light onto a patient's back in such a manner that the lines are substantially parallel to the vertical midline of the patient's body and border the midline on either side of the midline;
    means for detecting an image of the lines projected onto the patient's back and for generating a signal representing said image;
    signal processing means for enabling a comparison of the relative position of the lines in said detected image from said signal; and
    means for indicating an abnormality or lack of abnormality in the patient's spine from the comparison.

2. An apparatus according to claim 1, wherein said signal processing means includes means for effecting a continuous comparison of the relative positions of the lines versus time, whereby the patient can bend forward and said means for indicating will indicate any relative change in the position of the lines with time.

3. An apparatus according to claim 1, wherein said means for projecting and said means for detecting and generating include means for performing their respective functions at various forward bent postures of the patient.

4. An apparatus according to claim 1, wherein said means for detecting and generating includes a television camera, and said means for indicating includes a television monitor.

5. An apparatus according to claim 1, wherein each line of light is projected through a cylindrical lens.

6. An apparatus according to claim 1, wherein said means for projecting includes a laser.

7. An apparatus according to claim 5, wherein said means for projecting at least two lines of light includes means for dividing the light from a single light source into a plurality of light rays and means for projecting each ray through a respective said cylindrical lens.

8. An apparatus according to claim 1, wherein said means for detecting further includes a bandpass filter means for passing substantially only the wavelengths of said projected light to said means for detecting.

9. An apparatus according to claim 8, wherein said filter means is selectively positionable into or out of the imaging area of said means for detecting.

* * * * *